United States Patent [19]

Suli et al.

[11] Patent Number: 4,950,651
[45] Date of Patent: Aug. 21, 1990

[54] NITROSO-N-(β-CHLORO ETHYL)-CARBAMOYL PEPTIDES

[75] Inventors: Helga Suli; Kalman Medzihradszky; Hedvig Medzihradszky nee Schweiger; Karoly Lapis; Laszlo Kopper; Andras Jeney, all of Budapest, Hungary

[73] Assignee: Chinoin Gyogyszer es Vegyeszeti Termekek Gyara R.T., Budapest, Hungary

[21] Appl. No.: 725,146

[22] Filed: Apr. 19, 1985

Related U.S. Application Data

[63] Continuation of Ser. No. 435,748, Oct. 21, 1982, abandoned.

[30] Foreign Application Priority Data

Oct. 22, 1981 [HU] Hungary ............................. 3073/81

[51] Int. Cl.$^5$ ..................... A61K 37/02; A61K 37/24
[52] U.S. Cl. .................................... 514/18; 530/309; 530/312
[58] Field of Search .................. 260/112.5 R; 514/18; 530/312, 309

[56] References Cited

U.S. PATENT DOCUMENTS 3,814,746  6/1974  DeBarbieri ..................... 260/351.4

FOREIGN PATENT DOCUMENTS 2101226  3/1972  France .

OTHER PUBLICATIONS

Bulletin of the Chemical Society of Japan, vol. 48(4), 1333–1334 (1975), Machinami et al, Potential Antitumor N–Carbamoyl–N–Methyl–N–Nitroso Derivatives of Amino Acids=Chem. Abstracts (R).
Febs Letters, vol. 44, No. 2 (Aug. 1974), 160–163, Szekerke et al, A New Approach to the Study of the Contribution of Peptide Carriers to Antitumor Activity:-Binding of the Peptide Moiety to Human Serum Albumin=Chem. Abstracts (S).
J. Med. Chem. 6, 669–681 (1963), Johnston et al.
J. Med. Chem. 9, 892–911 (1966), Johnston et al.
Febs Letters, vol. 67, No. 1, (Aug. 1976), 45–47.
Helv. 58, 1528–1535 (1975).
Nature, 207, 1356–1359 (1956).
Eberle et al, Helv. Chim. Acta, vol. 58, 2106–2129 (1979).
Wieshahn et al, Nature, 292, Jul. 1981, pp. 467–469.
Legros et al, Cancer Res., 41, Apr. 1981, pp. 1539–1544.
Zeller et al, J. Cancer Res. Clin. Oncol., 95, 1979, pp. 43–49.
Stedman's Medical Dictionary, 24th Ed., p. 360, "Cytostatic".
Machinami et al, Chem. Abstracts, vol. 83, 1975, 43712q.
Szekerke, M. et al, Chem. Abstracts, vol. 83, 1975, 53244c.
DeBarbieri, Chem. Abstracts, vol. 78, 1973, 72600d.
Physician's Desk Reference, 41st Edition, pp. 759–760 and 2155–2156.
The Pharmacological Basis of Therapeutics, Goodman and Gilman, Fifth Edition, pp. 1250–1251 (1975).

Primary Examiner—Jacqueline Stone
Attorney, Agent, or Firm—Herbert Dubno; Jonathan Myers

[57] ABSTRACT

The invention relates to new peptide derivatives of the general Formula I

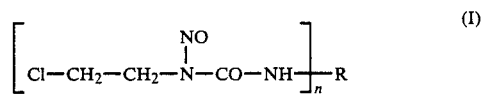

wherein
R is a group derived from any oligopeptide by removing a terminal amino group, or—if the oligopeptide comprises a diamino carboxylic acid—the amino group in the ω-position, or the terminal and ω-amino groups; and
stands for the integral number 1 or 2
and acid addition slats thereof and a process for the preparation thereof.

The new compounds of the general Formula I exhibit antitumor activity.

6 Claims, No Drawings

NITROSO-N-(β-CHLORO ETHYL)-CARBAMOYL PEPTIDES

This is a continuation of co-pending application Ser. No. 435,748 filed on Oct. 21, 1982, and now abandoned.

This invention relates to new N-nitroso-N-(β-chloro-ethyl)-carbamoyl peptides, a process for the preparation thereof and pharmaceutical compositions comprising the same.

According to a feature of the present invention there are provided new peptides of the Formula I

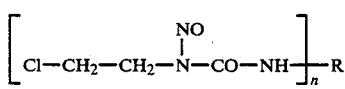

wherein

R is a group derived from any oligopeptide by removing a terminal amino group, or—if the oligopeptide comprises a diamino carboxylic acid—the amino group in the ω-position, or the terminal and ω-amino groups; and n stands for the integer 1 or 2 and acid addition salts thereof.

The acid addition salts of the compounds of the Formula (I) can be acid addition salts formed with therapeutically acceptable inorganic or organics acids.

It is known that the β-chloro-ethyl derivatives of N-nitroso-urea—e.g. the 1,3-bis-(β-chloro-ethyl)-1-nitroso-urea, BCNU [T. P. Johnston, G. S. McCaleb, J. A. Montgomery, J. Med. Chem. 6, 669 (1963)] and the 1-(β-chloro-ethyl)-1-nitroso-3-cyclohexyl-urea, CCNU [T. P. Johnston, G. S. McGaleb, P. S. Opliger, J. A. Montgomery, J. Med. Chem. 9 892 (1966)]—exhibit significant antitumor activity which enables the use of the said compounds in human therapy.

A common disadvantage of the nitroso-chloro-ethyl urea resides in the fact that the effective dose is extremely near to the toxic value. It is highly important to diminish the toxicity or increase the activity of the said compounds.

In principle the activity can be increased by preparing compounds which contain in addition to the cytostatic group also a molecule fragment which ensures that the molecule is bound to the cells of the tumor tissue with great affinity. Thus in a certain sense a specific effect takes place and a lower dose can be used which decreases the general toxicity of the compound.

Natural peptides—particularly polypeptide hormones—are bound to the receptors of the desired organ with a very large affinity. For this reason it can be expected that the affinity of the N-nitroso-N-(β-chloro-ethyl)-carbamoyl derivatives of the said natural peptides will also be significant but only and exclusively on the site capable of the recognition and identification of the structure of the peptide part. In this respect the complete peptide molecule is not needed and it is sufficient to select the fragment (active center) therefore bearing the characteristic biological effect. The only precondition of importance is that the substitution should not negatively influence the characteristic biological effect, i.e. the amino group to be substituted should not be necessary for the biological effect to be exerted. The fragments of α-melanotropine and the C-terminal tetrapeptide of gastrine possess—among others—the above property.

According to a further feature of the present invention there is provided a process for the preparation of the N-nitroso-N-(β-chloro-ethyl)-carbamoyl peptide derivatives of the Formula I and acid addition salts thereof which comprises (a) reacting a peptide of the general Formula II having a free amino group (wherein R' is a group derived from any oligopeptide by removing the terminal amino group, or—if the oligopeptide comprises a diamino carboxylic acid—the amino group in the ω-position, or the terminal and ω-amino groups, or is a derivative of a said group protected by a protecting group and n is as stated above) with the isocyanate of the Formula III (Cl—CH$_2$—CH$_2$—NCO) and nitrosating the compound of the Formula IV thus obtained

(wherein R' and n are as stated above); or (b) reacting a peptide of the Formula (II)

(wherein R' and n are as stated above) with an active ester of the Formula V

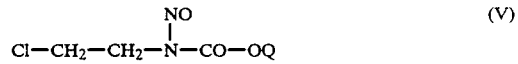

(Wherein Q is the group of an optionally substituted, active ester derived from a hydrocarbon, generally used in peptide chemistry);

and if desired removing the protecting gropus being present and if desired converting the compound thus obtained into its acid addition salt.

The protective group suitable for the process of the present invention is preferably the tert. butoxycarbonyl group. In the starting materials of the Formula V used in method (b) Q stands preferably for a phenyl group substituted by one or more electron-attracting groups.

According to a preferred embodiment of the process of the present invention one may proceed as follows:

The α-melanotropine is a polypeptide hormone formed from 13 amino acids. Smaller fragments thereof—among others the C-terminal tripeptide—maintain the characteristic biological effects of the hormone [Helv. 58, 1528, (1975); FEBS Letters 67, 45 (1976)]. The structure of the C terminal tripeptide is shown on Formula VI.

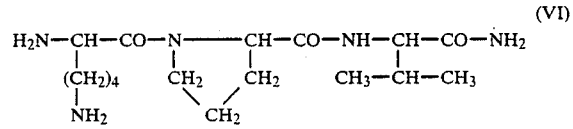

The tripeptide of the Formula VI contains two primary amino groups which can be converted into the corresponding N-nitroso-N-(β-chloro-ethyl)-carbamoyl derivatives by the methods described above. For this purpose the known tripeptide of the Formula VI is reacted with β-chloro ethyl-isocyanate and the α,ε-bis-(β-chloro-ethyl-carbamoyl)-tripeptide thus obtained is nitrosated with a nitrosating agent, preferably with sodium nitrite in the presence of an acid, or nitrosyl chloride or nitrogen trioxide etc. After nitrosation the bis-nitroso derivative of the Formula VII is obtained.

of the C-terminal tetrapeptide is shown by the Formula VIII.

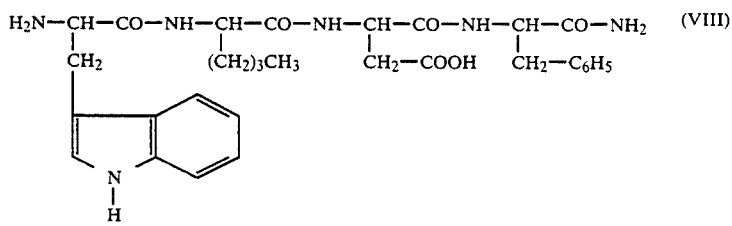

(VIII)

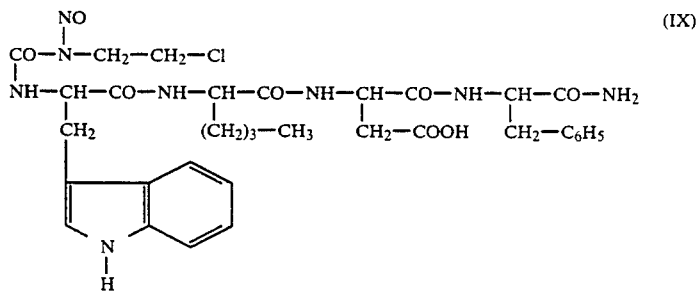

(VII)

The said known tetrapeptide [Nature 207, 1356, (1956)] can be converted into the corresponding N-nitroso-N-(β-chloro-ethyl)-carbamoyl derivative of the Formula IX (IX)

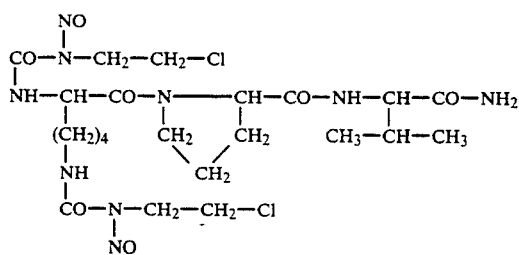

The bis-nitroso derivative of the Formula VII can also be prepared by reaction in a single step. The C-terminal tripeptide of the Formula VI is acylated with an active ester of N-nitroso-N-(β-chloro ethyl)-carbamic acid—preferably with the p-nitro-phenyl ester—in the presence of 1-hydroxy-benzotriazole.

The monocarbamoyl derivatives of the C-terminal tripeptide of the Formula VI can naturally be prepared by both methods; in this case one amino group of the tripeptide starting material bears a protecting group, preferably a tert. butoxycarbonyl group. After the formation of the substituted carbamoyl group, the protecting group can be selectively removed by known methods (e.g. by treatment with hydrochloric acid and formic acid).

Gastrine is a polypeptide hormone formed from 17 amino acids. The C-terminal tetrapeptide thereof—i.e. the norleucine analogue of same—possesses the characteristic biological effects of the hormone. The structure by the method described in connection with the fragment of melanotropine.

The pharmacological activity of the new compounds of the present invention are shown by test results, using α,ε-bis-[N-nitroso-N-(β-chloro-ethyl)-carbamoyl]-lysyl-prolyl-valine amide (referred to furtheron as Compound VII) and α-[N-nitroso-N-(βchloro-ethyl)-carbamoyl]-lysyl-prolyl-valine amide-hydrochloride (referred to as Compound X) as test compounds. The results obtained are summarized in the following Tables I and II.

In table I the effect of Compound X

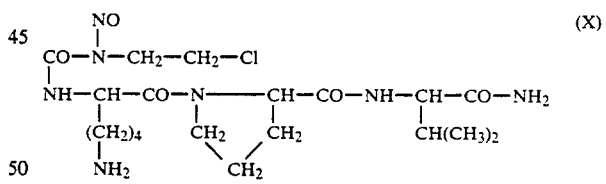

(X)

and VII on intraperitoneally implanted L-1210 leukemia is shown on mice. Both compounds X and VII proved to be more active than the 1,3-bis-(β-chloro-ethyl)-1-nitroso-urea (referred to furtheron BCNU and 2-[3-(2-chloro-ethyl)-3-nitroso-ureido]-2-deoxy-O-glycopyranose (referred to furtheron as Chlorosoticine) used as reference compounds.

TABLE I

| | Effect of Compounds X and VII on L-1210 leukemia | | | | |
|---|---|---|---|---|---|
| Test compound | Dose IP mg/kg | MST day | MST efficiency %, T/C | Average loss of weight on the 5th day, g | Number of live mice on the 5th [47th] day |
| BCNU | 40 | >47.0 | >783 | −1.4 | 6/6 (5) |
|  | 30 | >47.0 | >783 | −0.8 | 6/6 (5) |
| X | 150 | 10.5 | 175 | −1.1 | 6/6 (1) |
|  | 100 | >47.0 | >783 | −0.7 | 6/6 (3) |
|  | 65 | 29.5 | 492 | −0.5 | 6/6 (2) |

TABLE I-continued

Effect of Compounds X and VII on L-1210 leukemia

| Test compound | Dose IP mg/kg | MST day | MST efficiency %, T/C | Average loss of weight on the 5th day, g | Number of live mice on the 5th [47th] day | |
|---|---|---|---|---|---|---|
| | 40 | 13.0 | 217 | −0.7 | 6/6 | |
| VII | 200 | 8.5 | 142 | −1.5 | 6/6 | |
| | 130 | 12.0 | 200 | −0.6 | 6/6 | (2)+ |
| | 70 | >47.0 | ≧783 | −0.8 | 6/6 | (3) |
| | 40 | 14.0 | 233 | −0.3 | 6/6 | |
| Chlorosoticin | 48 | 8.5 | 142 | −1.3 | 6/6 | |
| | 32 | >47.0 | >783 | −1.2 | 5/6 | (3) |
| | 16 | 20.5 | 342 | −0.8 | 6/6 | |
| | 8 | 9.0 | 150 | +1.2 | 6/6 | |
| Control | physiological sodium chloride solution | 6.0 | — | +2.5 | 10/10 | |

+both mice are ill.
Tumor inoculum = $10^6$, ascites cells, i.p.
Host animal = CDF, female mice
Treatment = 3 days.
Toxicity = on the 5th day < 4/6 mice are alive.
Evaluation = MST = average survival period
Effect = T/C = $\frac{\text{MST treated}}{\text{MST control}} \times 100$
Critical limit = T/C ≧ 125, significant antitumor activity.

In Table II the pharmacological properties of Compound X are summarized:

TABLE II

Pharmacological properties of compound X
Toxic dose: 133–200 mg/kg i.p.
Mice infected with L-1210 are treated:

| Dosage mg/kg | ILS % | Number of surviving animals, after 40 days |
|---|---|---|
| 3 × 10 | ip 80% | |
| 3 × 50 | ip 150% | |
| 1 × 133 | ip — | 60% |
| 1 × 200 | toxical | |

TABLE III

Examination of the relation between the effect and the chemical structure with compounds similar to compound of formula X in mice suffering from $L_{1210}$ leukemia.

| Compound | Dosis mg/kg | ILS % |
|---|---|---|
| XI | 7 | 0 |
| | 28 | 10 |
| | 46 | 50 |
| | 100 | toxic |
| XII | 15 | 20 |
| | 45 | 10 |
| | 100 | 35 |
| | 150 | 230 |

The above data prove that the new peptide derivatives of the Formula X and VII are significantly more active and less toxic than the BCNU and Chlorosoticine used as control.

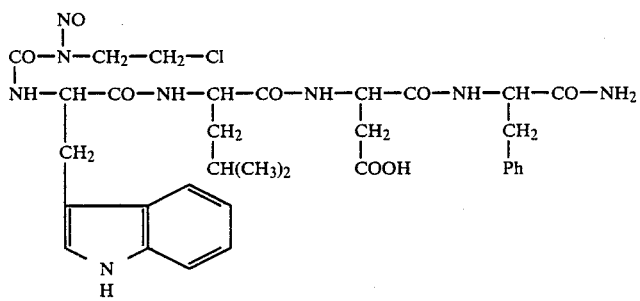
(XI)

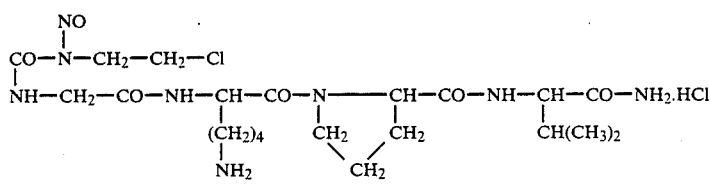
(XII)

TABLE IV

Effect of compound of formula X in combination with pharmaceuticals in mice suffering from L1210 leukemia

| | | Treatment | | |
|---|---|---|---|---|
| Compound | Dosis mg/kg | Day | ILS % | Surviving % |
| 1 X | 12.5 | 1 | 50 | |
| 2 X | 50.0 | 1 | 87 | |
| 3 BCNU | 5 | 1 | 25 | |
| 4 BCNU | 20 | 1 | 110 | |
| 5 treating corresponding to 2 + 3 | | | 325 | |
| 6 treating corresponding to 1 + 4 | | | 325 | |
| 7 X | 1 × 25 | 2 | 44 | |
| 8 cyclophosphamide | 1 × 50 | 2 | 44 | |
| 9 dibromodulcitol | 1 × 50 | 2 | 0 | |
| 10 BCNU | 1 × 10 | 2 | 77 | |
| 11 treatment corresponding to 7 + 8 | | | 77 | |
| 12 treatment corresponding to 7 + 9 | | | 44 | |
| 13 treatment corresponding to 7 + 10 | | | | 70 |
| 14 X | 1 × 50 | 3 | 33 | |
| 15 BCNU | 1 × 20 | 3 | 70 | |
| 16 treatment corresponding to 14 + 15 | | | | 60 |

TABLE V

Effect of compound of formula X on surviving mice suffering from L1210 leukemia

| | Treating | | | |
|---|---|---|---|---|
| Compound | Dosis mg/kg | Day* | ILS** | Surviving*** |
| X | 1 × 12.5 | 1 | 50 | |
| | 1 × 50 | 1 | 87 | |
| | 1 × 133- | 1 | | 40 |
| | 1 × 25 | 2 | 44 | |
| | 1 × 25 | 3 | 33 | |
| | 1 × 100 | 3 | 45 | |
| | 3 × 10 | 1,5,9 | 80 | |
| | 3 × 50 | 1,5,9 | 250 | |
| | 4 × 10 | 1,2,5,6 | 110 | |

*i.p. administration on the day noted after transplantation

**ILS % = $\dfrac{\text{surviving time of mice untreated} - \text{those untreated}}{\text{surviving time of mice treated}} \times 100$

***surviving on the 60th day after transplantation

TABLE VI

Effect of X on solid tumors (A) S180 mice tumor (s.c.)

The dosis of 100 mg/kg or 5 × 20 mg/kg i.p. (treating from the day after transplantation) is ineffective.

(B) Lewis lung and B16 melanoma - metastatizing mice tumor (i.m.)

| | Lewis tumor | | B16 melanoma | |
|---|---|---|---|---|
| Treating | Median surviving day | ILS % | Median surviving day | ILS % |
| control (X) | 21.0 | — | 26.0 | — |
| 100 mg/kg | 22.0 | 4 | 31.5 | 21.5 |
| 5 × 20 mg/kg | 27.0 | 29 | 35.0 | 35 |
| BNCU | | | | |
| 20 mg/kg | 28.5 | 36 | 42.0 | 61 |
| 5 × 4 mg/kg | 25.0 | 19 | 34.0 | 31 | i.p. administration from the 1st day after transplantation (C) Human tumor xenografts (s.c.)

HT18 (amelanoticus melanoma)

| | | |
|---|---|---|
| Control - median TD | 22.5 days | |
| 100 mg/kg | >50.0 days | GD = 1.0 |
| 5 × 20 mg/kg | 56.25 days | 1.5 |

HT22 (mucinosus colon carcinoma)

| | | |
|---|---|---|
| Control | 17.0 days | |
| 100 mg/kg | 24.0 days | 0.29 |
| 5 × 20 mg/kg | 21.5 days | 0.26 |

HT17 (adenomatosus colon carcinoma)

| | | |
|---|---|---|
| Control | 16.5 days | |
| 100 mg/kg | 14.75 days | 0.0 |
| 5 × 20 mg/kg | 15.0 | 0.0 |

Time of treating: having a tumor of ca. 8 mm³
Way of treating: i.p.
TD = duplication of the tumor volume GD = delay of growing = $\dfrac{TD_{Ke} - TD_{Ko}}{TD_{Ko}}$ Ke = treated
Ko = control According to a still further feature of the present invention there are provided pharmaceutical compositions comprising as active ingredient at least one compound of the Formula I or an acid addition salt thereof and inert solid or liquid pharmaceutical carriers. The said pharmaceutical compositions contain usual pharmaceutical carriers and auxiliary agents and can be prepared by methods of pharmaceutical industry known per se. The compositions may be finished e.g. in the form of tablets, capsules, ampoules etc.

Further details of the present invention are to be found in the following Examples, without limiting the scope of protection to the Examples.

EXAMPLE 1

α,ε-bis-(β-chloro-ethyl-carbamoyl)-lysyl-prolyl-valine amide 736 mg of (1.6 millimoles) of lysyl-propyl-valine amide-diacetate [Helv. 58, 2106 (1978)] are dissolved in 8 ml of dimethyl formamide and cooled to 0° C. 0.46 g ml (3.2 millimoles) of triethyl amine and 0.34 ml (4 millimoles) of β-chloro-ethyl-isocyanate are added dropwise. The reaction mixture is stirred at 0° C. for 4 hours, thereafter allowed to stand and distilled off in vacuo. The residue is admixed with water, the precipitated product is filtered off and dried. Thus 480 mg of the named compound are obtained, yield 54%. Mp.: 183°–185° C.; $R_F$=0.75 (a 4:1:1:1 mixture of n-butanol, pyridine, glacial acetic acid and water; TLC Kieselgel G, Merck).

| $C_{22}H_{39}N_7O_5Cl_2$ (552.5) | | | | |
|---|---|---|---|---|
| calculated: | C: 47.82% | found: | C: 47.90% |
| | H: 7.11% | | H: 7.60% |
| | N: 17.74% | | N: 17.41% |
| | Cl: 12.83% | | Cl: 13.26%. |

EXAMPLE 2

α,ε-bis-[N-nitroso-N-(β-chloro-ethyl)-carbamoyl]-lysyl-prolyl-valine amide 460 mg (1 millimole) of lysyl-prolyl-valinamide-diacetate [Helv. 58, 2106, 1978)] are dissolved in 6 ml of dimethyl formamide, whereupon 0.28 ml (2 millimoles) of triethyl amine and 548 mg (2 millimoles) of N-nitroso-β-chloro-ethyl carbamoyl-p-nitro-phenol and thereafter 270 mg (2 millimoles) of 1-hydroxy-benzotriazole are added. After 2 hours the dimethyl formamide is distilled off in vacuo, the residue is dissolved in 30 ml of ethyl acetate and extracted with water. The ethyl acetate phase is dried and evaporated. The residue is treated with anhydrous ether, the ether is decanted off and the oil is dried. The solid foam thus formed is purified on a column filled with silica gel. The fractions are collected and the solvent is distilled off in vacuo. The residue is powdered in the presence of anhydrous petrolether and filtered. Thus 312 mg of the named compound are obtained, yield 51%.

Named compound: $R_F=0.80$ (a 1:3 mixture of methanol and ethyl acetate, TLC Kieselgel G Merck);

Starting material: $R_F 0.88$ (a 240:20:6:11 mixture of ethyl acetate, pyridine, glacial acetic acid and water, TLC Kieselgel G, Merck). $\epsilon=185$ (N-nitroso group, 397 nm).

| $C_{22}H_{37}N_9O_7Cl_2$ (611.51) | | | |
|---|---|---|---|
| Calculated: | Cl: 11.59% | Found: | Cl: 11.18% |
| | N: 20.61% | | N: 20.07% |

EXAMPLE 3

α,ε-bis-[N-nitroso-N-(β-chloro-ethyl)-carbamoyl]-lysyl-prolyl-valine amide

To 552 mg (1 millimole) of α,ε-bis-(β-chloro-ethyl-carbamoyl)-lysyl-prolyl-valine amide 10 ml of 99% formic acid are added whereupon a solution of 500 mg sodium nitrite and 3 ml of a water is added dropwise within an hour. Next day the reaction mixture is evaporated in vacuo. The residue is treated with water, filtered and washed with water. Thus 460 mg of the named compound are obtained, yield 75%.

$R_F=0.80$ (a 1:3 mixture of methanol and ethylacetate, TLC, Kieselgel Merck).

$\epsilon=184$ (N-nitroso group, 397 nm).

| $C_{22}H_{37}N_9O_7Cl_2$ (611.51) | | | |
|---|---|---|---|
| Calculated: | Cl: 11.59% | Found: | Cl: 11.41% |
| | N: 20.61% | | N: 20.10% |

EXAMPLE 4

α-N-nitroso-N-(β-chloro-ethyl)-carbamoyl-ε-tert. butyloxycarbonyl-lysyl-prolyl-valine amide 614 mg (1 millimole) of ε-tert. butoxycarbonyl-lysyl-prolyl-valine amide tosylate [Helv. 46, 870 (1963)] are dissolved in 10 ml of anhydrous dimethyl formamide, whereupon 0.14 ml (1 millimole) of triethyl amine, 274 mg (1 millimole) of N-nitroso-β-chloro-ethyl-carbamoyl-p-nitro-phenol and 136 mg (1 millimole) of 1-hydroxy-benzotriazole are added and the reaction is carried out in an analogous manner to Example 2. Thus 250 mg of the named compound are obtained, yield 43%.

Named compound $R_F=0.90$ (a 9:1 mixture of chloroform and methanol, TLC Kieselgel G, Merck).

Starting material: $R_F=0.80$ (a 4:1:1 mixture of n-butanol, glacial acetic acid and water, Kieselgel G, Merck). $\epsilon=90$ (N-nitroso-group, 397 nm).

| $C_{24}H_{42}N_7O_7Cl$ (576.10) | | | |
|---|---|---|---|
| Calculated: | Cl: 6.15% | Found: | Cl: 6.00% |

| $C_{24}H_{42}N_7O_7Cl$ (576.10) | | | |
|---|---|---|---|
| | N: 17.02% | | N: 16.61% |

(b)
α-[N-nitroso-N-(β-chloro-ethyl)-carbamoyl]-lysyl-prolyl-valinamide-hydrochloride 200 mg of α-[N-nitroso-n-(β-chloro-ethyl)-carbamoyl]-ε-tert. butoxycarbonyl-lysyl-prolyl-valine amide are admixed with 6 ml of 0.17N formic acid in hydrochloric acid, the solution is allowed to stand for 5 minutes and thereafter evaporated. The residue is dissolved in water, and extracted with ethyl acetate. The aqueous layer is lyophilized. Thus 140 mg of the named compound are obtained.

$R_F=0.10$ (a 4:1:1 mixture of n-butanol, glacial acetic acid and water, Kieselgel G, Merck).

| $C_{19}H_{35}N_7O_5Cl_2$ (512.44) | | | |
|---|---|---|---|
| Calculated: | Cl: 13.84% | Found: | Cl: 13.72% |
| | N: 19.13% | | N: 18.81% |
| | ε: 88 (N-nitroso-group, 397.nm) | | |

EXAMPLE 5

β-chloro-ethyl-carbamoyl-tryptophyl-norleucyl-α-asparagyl-phenyl-alaninamide 615 mg (1 millimole) of tryptophyl-norleucyl-α-asparagyl-phenylalanine amide hydrochloride [Nature 207, 1356 (1956)] are dissolved in 6 ml of anhydrous dimethyl formamide, whereupon 0.14 ml (1 millimole) of triethyl amine and 0.1 ml (1.2 β-chloro-ethyl-isocyanate and the reaction is carried out in analogous manner to Example 1. Thus 600 mg of the named compound are obtained, yield 88%.

Mp.: 201°–202° C.

| $C_{33}H_{42}N_7O_7Cl$ (684.19) | | | |
|---|---|---|---|
| Calculated: | Cl: 5.18% | Found: | Cl: 4.94% |
| | N: 14.33% | | N: 13.78% |

EXAMPLE 6

N-nitroso-N-(β-chloro-ethyl)-carbamoyl-tryptophyl-norleucyl-α-asparagyl-phenyl-alaninamide are reacted with a solution of 300 mg of sodium nitrite and 2 ml of water in an analogous manner to Example 3. Thus 605 mg of the named compound are obtained, yield 85%.

$R_F=0.80$ (a 4:1:1 mixture of n-butanol, glacial acetic acid and water, Kieselgel G, Merck).

| $C_{33}H_{41}N_8O_8Cl$ (713.20) | | | |
|---|---|---|---|
| Calculated: | Cl: 4.97% | Found: | Cl: 4.73% |
| | N: 15.71% | | N: 15.28% |
| | NO: 4.20% | | NO: 3.87% |

Since in the absorption interval of the nitroso group there is an absorption of the peptide, per se, in this Example the nitroso group is determined by the method of Loo and Dion [J. Pharm Sci. 54, 809, (1965)].

EXAMPLE 7

N-nitroso-N-(β-chloro-ethyl)-carbamoyl-tryptophyl-norleucyl-α-asparagyl-phenylalanine-amide 921 mg (1.5 millimoles) of tryptophyl-norleucyl-α-asparagyl phenylalanin-amide-hydrochloride [Nature 207, 1356 (1956)], 0.21 ml (1.5 millimoles) of triethyl amine, 420 mg (1.5 millimoles) of N-nitroso-β-(chloro-ethyl-carbamoyl)-p-nitro-phenol and 200 mg (1.5 millimoles) of 1-hydroxy-benzotriazole are reacted in an analogous manner to Example 2. Thus 800 mg of the named compound are obtained, yield 75%.

$R_F = 0.80$ (a 4:1:1 mixture of n-butanol, glacial acetic acid and water, Kieselgel Merck).

| $C_{33}H_{41}N_8O_8Cl$ (713.20) | | | |
|---|---|---|---|
| Calculated: | Cl: 4.97% | Found: | Cl: 4.58% |
| | N: 15.71% | | N: 15.32% |
| | NO: 4.20% | | NO: 3.92% |

The nitroso group is determined by the method referred to in Example 6.

EXAMPLE 8

N-nitroso-N-(β-chloro-ethyl)-carbamoyl-glutamyl-histidyl-phenylalanyl-arginyl-tryptophyl-glycine 332 mg (0.4 millimoles) of glutamyl-histidyl-phenylalanyl-arginyl-tryptophyl-glycine [Helv. Chim. Acta 44, 1991, (1961)], 0.056 ml of triethyl amine, 120 mg (0.44 millimole) of N-nitroso-β-chloro-ethyl-carbamoyl-p-nitro-phenol and 56 mg (0.4 millimole) of 1-hydroxy-benzotriazole are reacted in an analogous manner to Example 2. Thus 133 mg of the title compound are obtained.

$R_F = 0.55$ (a 70:5:25 mixture of methanol, acetone and water).

| $C_{42}H_{53}N_{14}O_{11}Cl$ (965.43) | | | |
|---|---|---|---|
| Calculated: | Cl: 3.67% | Found: | Cl: 3.22% |
| | N: 20.31% | | N: 19.98% |
| | NO: 3.10% | | NO: 2.81% |

The nitroso group is determined by the method referred to in Example 6.

EXAMPLE 9

A lyophilized powder ampoule containing 10 mg of α-[N-nitroso-N-(β-chloro-ethyl)-carbamoyl]-lysyl-prolyl-valinamide-hydrochloride The powder ampoule comprises 10 mg of α-[N-nitroso-N-(β-chloro-ethyl)-carbamoyl]-lysyl-prolyl-valinamide-hydrochloride (pro powder ampoule).

The solvent ampoule comprises 300 mg of sorbitol and ad 2 ml of aqua des. pro. inj. (pro ampoule).

A solution having a concentration of 5 g of active ingredient per liter is prepared. The said solution is sterilized by filtration, filled into ampoules and cryodehydrated in a known manner. The powder ampoules are sealed with a rubber cap and a metal seal under sterile conditions and signed. The powder ampoule is packed together with a solvent ampoule containing 15 g of a 1% aqueous sorbitol solution.

EXAMPLE 10

Capsules comprising 100 mg of α,ε-bis-[N-nitroso-N-(β-chloro-ethyl)-carbamoyl]-lysyl-prolyl-valinamide The composition of a capsules is as follows:

| Component | Amount, mg |
|---|---|
| α,ε-bis-[N-nitroso-N-(β-chloro-ethyl)--carbamoyl]-lysyl-prolyl-valinamide | 100 |
| Carbowax | 5 |
| Talc | 5 |

The crystalline active ingredient is admixed with a mixture of Carbowax and talc previously homogenized into a fine powder. The granules thus obtained are filled into hard gelatine capsules (total weight 110 mg) by using a suitable apparatus.

EXAMPLE 11

Intestinosolvent Capsule

The capsules prepared according to Example 10 are coated with an intestinosolvent layer by methods known per se.

EXAMPLE 12

N-Nitroso-N-(β-chloro-ethyl)-carbamoyl-tryptophyl-leucyl-α-asparagyl-phenylalanine-amide (XI)

(a) 633 mg (1 mmole) of tryptophyl-leucyl-α-asparagyl-(β-terc-butyl-ester)-phenylalanine-amide [Z. Physiol-Chem. 353 1246 (1972)] are allowed to stand in 6 ml of 2n ethyl acetate in hydrochloric acid then ether is added, the crystalls precipitating are filtered off and washed with ether. 590 mg (93%) of the named product are obtained.

$R_F = 0.74$ (butanol-pyridine-glacial acetic acid-water=30:20:6:24, Kieselgel G, Merck).

(b) 921 mg (1.5 mmoles) of tryptophyl-leucyl-α-asparagyl-phenylalaninamide-hydrochloride are dissolved in 10 ml of abs. dimethyl formamide, then 373 mg (1.5 mmoles) of N-nitroso-β-chloro-ethyl-carbamoyl-N-hydroxy-succinimide and 0.42 ml (3 mmoles) of triethyl amine are added. After stirring for 15 minutes the dimethyl formamide is distilled off in vacuo. The residue is scuffed with water, filtered off and washed with water. 980 mg (92%) of the named product are obtained.

$R_F = 0.69$ (ethyl acetate-pyridine-glacial acetic acid-water=30:20:6:11, Kieselgel G, Merck).

| $C_{33}H_{41}N_8O_8Cl$ (713.20) | | | |
|---|---|---|---|
| Calculated: | Cl: 4.97% | found: | Cl: 4.58% |
| | N: 15.71% | | N: 15.32% |
| | NO: 4.20% | | NO: 3.95% |

EXAMPLE 13

(a)

α-N-nitroso-N-(β-chloro-ethyl)-carbamoyl-ε-tert-butyloxycarbonyl-glycyl-lysyl-prolyl-valine-amide 1.30 g (2.6 mmoles of ε-tert-butyloxycarbonyl-glycyl-lysyl-prolyl-valine-amide [Clin. Endrocrinol 5 41s (1976)] are dissolved in 13 ml of abs dimethyl formamide then 650 mg (2.6 mmoles) of N-nitroso-β-chloro-ethyl-carbamoyl-N-hydroxy-succinimide and 0.36 ml (2.6 mmoles) of triethyl amine are added. After stirring for 15 minutes the reaction mixture is evaporated in vacuo. The residue is dissolved in ethyl acetate and extracted with water. The ethyl acetate phase is dried and evaporated. 1.29 g (80%) of the named product are obtained.

$R_F=0.82$ (chloroform-methanol=8:2, Kieselgel G, Merck).

| $C_{16}H_{45}N_8O_8Cl$ (633.16) | | | |
|---|---|---|---|
| Calculated: | Cl: 5.60% | Found: | Cl: 5.48% |
| | N: 17.69% | | N: 17.31% |
| | $\epsilon$: 91 (N-nitroso group, 397 nm) | | |

(b)

α-N-nitroso-N-(β-chloro-ethyl)-carbamoyl-glycyl-lysyl-prolyl-valine-amide-hydrochloride (XII)

633 mg (1 mmole) of α-N-nitroso-N-(β-chloro-ethyl)-carbamoyl-ε-tert-butyloxycarbonyl-glycyl-lysyl-prolyl-valine-amide are allowed to stand for 5 minutes in 10 ml of 0.14n formic acid in hydrochloric acid then the solution is evaporated. The residue is dissolved in water, extracted with ethyl acetate. The aqueous phase is lyophilized. 540 mg (95%) of the named product are obtained.

$R_F=0.65$ (ethyl acetate-pyridine-formic acid-water=60:20:6:5,5, Kieselgel G, Merck).

| $C_{21}H_{38}N_8O_6Cl_2$ (569.59) | | | |
|---|---|---|---|
| Calculated: | Cl: 12.45% | Found: | Cl: 12.01% |
| | N: 19.67% | | N: 18.87% |
| | $\epsilon = 84$ (N-nitroso group, 396 nm) | | |

What we claim is:

1. A compound of the Formula (I)

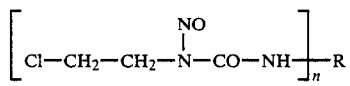

wherein

R is an oligopeptide group having its N-terminal amino group removed and selected from the group which consists of:
Lys-Pro-Val-NH$_2$,
Trp-Leu-Asp-Phe-NH$_2$, and
Gly-Lys-Pro-Val-NH$_2$; and n is 1; or R is Lys-Pro-Val-NH$_2$, wherein the Lys residue has both its N-terminal and ω-amino groups removed, and n is 2; or a pharmaceutically acceptable acid addition salt thereof formed with a therapeutically acceptable inorganic or organic acid.

2. A compound of the Formula (I)

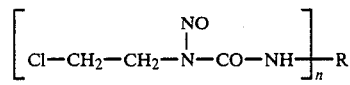

wherein

R is an oligopeptide group having its N-terminal amino group removed which is:
Lys-Pro-Val-NH$_2$, and n is 1; or R is Lys-Pro-Val-NH$_2$, wherein the Lys residue has both its N-terminal and ω-amino groups removed, and n is 2; or a pharmaceutically acceptable acid addition salt thereof formed with a therapeutically acceptable inorganic or organic acid.

3. α,ε-bis-[N-nitroso-N-(β-chloro-ethyl)-carbamoyl]-lysyl-prolyl-valine amide as defined in claim 2.

4. α,ε-bis-[N-nitroso-N-(beta-chloroethyl)-carbamoyl]-lysyl-proplyl-valine amide or a pharmaceutically acceptable acid addition salt thereof formed with a therapeutically acceptable inorganic or organic acid as defined in claim 2.

5. A pharmaceutical composition effective against L-1210 leukemia which comprises a therapeutically effective amount of a compound of the Formula (I) as defined in claim 1 or a pharmaceutically acceptable inorganic or organic acid addition salt thereof in admixture with a pharmaceutically acceptable inert carrier.

6. A method of treatment effective against L-1210 leukemia in a mammalian subject which comprises the step of intraperitoneally administering a therapeutically effective amount of the compound of the Formula (I) defined in claim 1 or a pharmaceutically acceptable acid addition salt thereof formed with a therapeutically acceptable inorganic or organic acid.

* * * * *